United States Patent [19]
Van Arsdell et al.

[11] Patent Number: 5,541,084
[45] Date of Patent: Jul. 30, 1996

[54] HYBRID YEAST PROMOTER COMPRISING AN ENO2 UAS AND TATA REGION AND AN ADDITIONAL UAS LOCATED BETWEEN SAID ENO2 UAS AND TATA REGION

[75] Inventors: Scott Van Arsdell, Cambridge, Mass.;
Robert S. Daves, Syracuse, N.Y.;
Robert R. Yocum, 180 Jason St.,
Arlington, Mass. 02174

[73] Assignee: Robert R. Yocum, Lexington, Mass.

[21] Appl. No.: 898,351

[22] Filed: Jun. 12, 1992

Related U.S. Application Data

[63] Continuation of Ser. No. 203,313, Jun. 6, 1988, abandoned, which is a continuation-in-part of Ser. No. 58,818, Jun. 5, 1987, abandoned.

[51] Int. Cl.⁶ .............. C12N 9/30; C12N 15/09; C12N 15/81; C12N 1/19
[52] U.S. Cl. ........... 435/69.1; 435/172.3; 435/254.11; 435/254.2; 435/254.21; 435/320.1; 536/23.1; 536/23.2; 536/23.7; 536/24.1
[58] Field of Search ................ 435/69.1, 72.3, 435/254.11, 254.2, 254.21, 320.1; 935/37, 41, 44, 69; 536/23.1, 24.1, 23.2, 23.7

[56] References Cited

U.S. PATENT DOCUMENTS 4,727,028  2/1988  Santerre et al. .............. 435/240.2
4,876,197  10/1989  Brake et al. .................. 735/172.3

OTHER PUBLICATIONS

Lorch et al. J. Mol. Biol. (1985) 186:821–824.
Velati–Bellini et al. Appl. Microbiol. Biotechnol. 25:124–131 (1986) Biosis Abstract #83085261.
Biotech Abstr. #87–00748 WO 8606077, Oct. 23, 1986.
Biotech. Abstr. #85–03745 EP 132309, Jan. 30, 1985.
Uemura et al. (1985) J. Biochem. 98:859–862.
Innis et al. (1985) Science 228: 21–26.
Guarente et al. (1982) Proc. Natl. Acad. Sci. 79:7410–7414.
Holland et al. (1981) J. Bio. Chem. 256 3: 1385–1395.
Cohen et al. (1986) Mol. & Cell Bio. 2287–2297.
Carlson et al. (1982) Cell 28: 145–154.
Guarente et al. (1984) Proc. Natl. Acad. Sci. 81: 7860–7864.

*Primary Examiner*—John L. LeGuyader
*Attorney, Agent, or Firm*—Fish & Richardson P.C.

[57] ABSTRACT

A DNA sequence having a yeast ENO2 promoter functionally fused to a heterologous gene.

15 Claims, 3 Drawing Sheets

FIG. 3

```
                                                        GATCTGAGCT TTA
                                                         ACTCGA    AAT

GCCTAAAAAA  ACCTTCTCTT  TGGAACTTTC  AGTAATACGC  TTAACTGCTC
CGGATTTTTT  TGGAAGAGAA  ACCTTGAAAG  TCATTATGCG  AATTGACGAG

ATTGCTATAT  TGAAGTACGG  ATTAGAAGCC  GCCGAGCGGG  TGACAGCCCT
TAACGATATA  ACTTCATGCC  TAATCTTCGG  CGGCTCGCCC  ACTGTCGGGA

CCGAAGGAAG  ACTCTCCTCC  GTGCGTCCTC  GTCTTCACCG  GTCGCGTTCC
GGCTTCCTTC  TGAGAGGAGG  CACGCAGGAG  CAGAAGTGGC  CAGCGCAAGG

TGAAACGCAG  ATGTGCCTCG  CGCCGCACTG  CTCCGAACAA  TAAAGATTCT
ACTTTGCGTC  TACACGGAGC  GCGGCGTGAC  GAGGCTTGTT  ATTTCTAAGA

ACAATACTAG  CTTTTATGGT  TATGAAGAGG  AAAAATTGGC  AGTAACCTGG
TGTTATGATC  GAAAATACCA  ATACTTCTCC  TTTTTAACCG  TCATTGGACC

CCCCACAAAC  CTTCAAATGA  ACGAATCAAA  TTAACAACCA  TAGGATGATA
GGGGTGTTTG  GAAGTTTACT  TGCTTAGTTT  AATTGTTGGT  ATCCTACTAT

ATGCGATTAG  TTTTTTAGCC  TTATTCTGG   GGTAATTAAT  CAGCGAAGCG
TACGCTAATC  AAAAAATCGG  AATAAGACC   CCATTAATTA  GTCGCTTCGC

|
ATGATTTTTG  ATC  TCGGCA
TACTAAAAAC  TAG  AGCCGTCTAG
```

HYBRID YEAST PROMOTER COMPRISING AN ENO2 UAS AND TATA REGION AND AN ADDITIONAL UAS LOCATED BETWEEN SAID ENO2 UAS AND TATA REGION

This is a continuation of application Ser. No. 07/203,313, filed Jun. 6, 1988, now abandoned, which is a continuation-in-part of Ser. No. 07/058,818 filed Jun. 5, 1987, now abandoned.

BACKGROUND OF THE INVENTION

This invention relates to genetic engineering of yeast, and to the use of certain promoters to improve the results of such genetic engineering.

One of the goals of genetic engineering in yeast is to construct strains of yeast that produce large amounts of a desired protein or enzyme. A particular protein or enzyme may be of interest as a product itself (for example, human alpha interferon), or a protein or enzyme may be of interest because it facilitates production by the host yeast of a desired metabolite (for example, ethanol or an amino acid) or production of a food or beverage product (for example, beer, wine, bread, or spirits). Although it is now routine to obtain some level of expression in yeast of any desired gene into its corresponding protein, the attainment of levels of expression high enough to allow a process to be performed profitably is often difficult.

The term "promoter", as used in connection with the expression of genes in yeast, has a meaning broader than the meaning of the term when used in connection with *E. coli*, the organism for which promoters were first described. The term "promoter", as used herein, means any DNA sequence which, when associated with a structural gene in a host yeast cell, increases, for that structural gene, one or more of 1) transcription, 2) translation, or 3) mRNA stability, compared to transcription, translation, or mRNA stability in the absence of the promoter sequence, under appropriate growth conditions (e.g., if the promoter is inducible, in the presence of the inducing substance). "mRNA stability" means longer half-life of mRNA.

Several strong promoters are known in the art and have been shown to be useful for expression of heterologous genes in yeast. (A "heterologous gene" means any gene that is not naturally functionally associated with a given promoter, whether that gene is derived from yeast or not.) For example, promoters naturally associated with the *Saccharomyces cerevisiae* genes TPI1 (triose phosphate isomerase), PGK1 (phosphoglycerate kinase), PYK1 (pyruvate kinase), TDH1, TDH2, and TDH3 (glyceraldehyde phosphate dehydrogenase or triose phosphate dehydrogenase), and ENO1 (enolase 1) have been described as useful for expression of heterologous genes in yeast (Kawasaki, U.S. Pat. No. 4,599,311; Kingsman and Kingsman, U.S. Pat. No. 4,615,974; Burke et al., EPO patent application Ser. No. 84300091.0; and Nunberg et al., WPO patent application Ser. No. 84/02921). All of the above genes encode enzymes which are involved in the glycolytic pathway of yeast, and which are among the most abundant enzymes in the yeast cytoplasm (Brousse et al. (1985) Applied and Environmental Microbiology 50: 951).

Some yeast strains have two different enzymes which act as enolases in the glycolytic pathway. In *S. cerevisiae*, these two enzymes have been given the names enolase 1 and enolase 2, which are encoded by the ENO1 and ENO2 genes, respectively, each of which has associated with it its distinct promoter sequences (Holland et al. (1980) J. Biol. chem. 257: 7181 and Cohen et al. (1986) Mol. Cell Biol. 6: 2287). In *S. cerevisiae*, using glucose as a carbon source, enolase 2 is more abundant than enolase 1. As used herein, "enolase 2" refers to the most abundant enolase of any yeast strain using glucose as a carbon source, and "ENO2 promoter" refers to a promoter sequence naturally associated with the gene encoding the most abundant enolase in a yeast strain using glucose as a carbon source.

There have been some attempts to make hybrid yeast promoters. For example, Kingsman et al., EPO 258 067, describe work in which substitution of the PGK UAS with the GAL1,10 UAS confers galactose regulation on the PGK promoter, but insertion of the GAL1,10 UAS at a site upstream or downstream from the PGK UAS, so that both PGK and GAL1,10 UAS's were present in the promoter sequence, did not result in galactose regulation of PGK gene expression.

SUMMARY OF THE INVENTION

In general, the invention features a DNA sequence including a yeast ENO2 promoter functionally fused to a heterologous gene, and a yeast cell transformed with that sequence. ("Functionally fused" means that transcription, translation, or mRNA stability of the heterologous gene is affected by the ENO2 promoter.) Generally, the DNA sequence of the invention is contained in a plasmid vector used to transform a host yeast cell, which is cultured to produce the protein or enzyme encoded by the heterologous gene. A preferred enzyme is a glucoamylase, which enables host yeast cells (preferably of the genus Saccharomyces) to utilize polysaccharides and thus renders the host yeast cells useful in the production of low carbohydrate "light" beer as described in Yocum et al. U.S. Ser. No. 864,785, assigned to the same assignee as the present application, hereby incorporated by reference.

ENO2 promoters can cause high heterologous gene expression levels in host yeast cells. In addition, ENO2 promoter sequences of *S. cerevisiae* have the advantage of being regulatable: expression can be repressed 20-fold by growing the yeast on a nonfermentable carbon source, such as glycerol, lactate or ethanol (Cohen et al. (1986) Mol. Cell Biol. 6: 2287). Thus, in a case where the heterologous gene encodes a protein or enzyme inhibitory to yeast growth, expression of that gene can be repressed, to allow the cell mass to accumulate by growing the cells on a nonfermentable carbon source, and then expression of the desired gene induced by addition of glucose to the growth medium.

The invention also features a DNA sequence including a hybrid yeast promoter functionally fused to a heterologous gene, as well as a host yeast cell transformed with that sequence. The hybrid yeast promoter includes ENO2 promoter DNA functionally fused to a DNA sequence that contains a first UAS derived from a yeast promoter. Preferably, the ENO2 promoter DNA includes an ENO2 TATA region and an ENO2 UAS, and the first UAS may be derived from a yeast promoter other than the ENO2 yeast promoter or, alternatively, from an ENO2 promoter. The first UAS is located between the ENO2 UAS and the ENO2 TATA region. Most preferably, the first UAS derived from the non-ENO2 yeast promoter is a GAL1,10 UAS derived from the GAL1,10 DNA sequence of *S. cerevisiae*. In any given yeast strain, the GAL1,10 UAS is a DNA sequence located between the GAL1 yeast gene encoding galactokinase, and the GAL1,10 yeast gene, encoding UDP-galactose epimerase. The GAL1,10 UAS regulates both genes, which are divergently transcribed. GAL1,10 UAS's from other yeast species, particularly Saccharomyces yeasts such as *S. carlsbergensis*, can also be used. The DNA sequence of the *S. carlsbergensis* GAL1,10 UAS (Citron et al. (1984) J. Bact. 158: 269) is about 95% homologous with the DNA sequence of the GAL1,10 UAS of *S. cerevisiae*.

Hybrid yeast promoters of the invention are useful for achieving high heterologous gene expression in host yeast cells, and for allowing for the hybrid promoter to be regulated by a different carbon source; e.g., whereas the ENO2 promoter is normally induced by glucose, the hybrid ENO2-GAL1,10 promoter is repressed by glucose and induced by galactose.

Other features and advantages of the invention will be apparent from the following description of the preferred embodiments thereof, and from the claims.

DESCRIPTION OF THE PREFERRED EMBODIMENT

The drawings are first described.

Drawings

Figure 1:
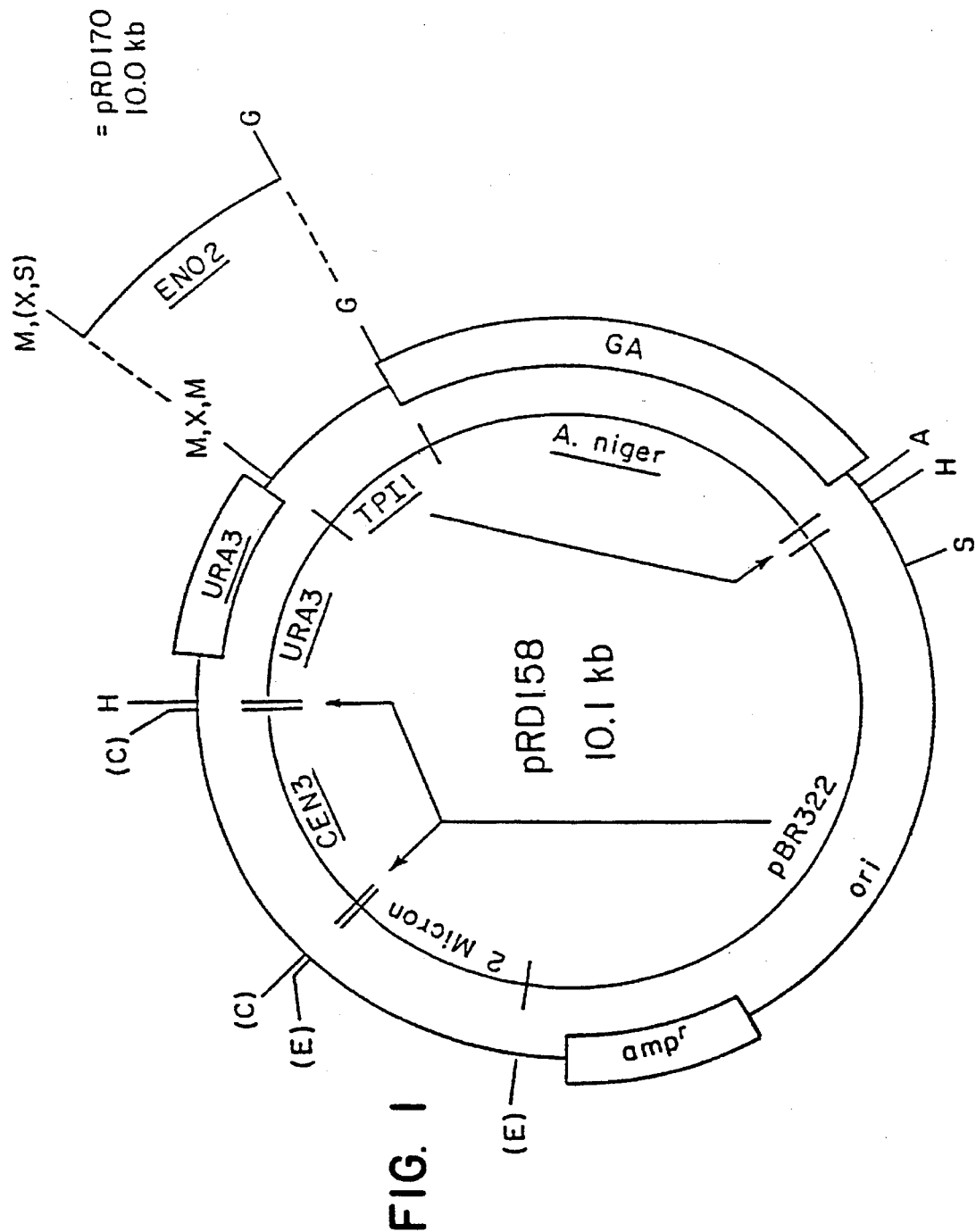

FIG. 1 is a diagrammatic representation of a plasmid, pRD158, containing a glucoamylase gene under the transcriptional control of the prior art TPI1 promoter, and the derivation of the ENO2 promoter-containing plasmid, pRD170, of the invention from pRD158.

Figure 2:
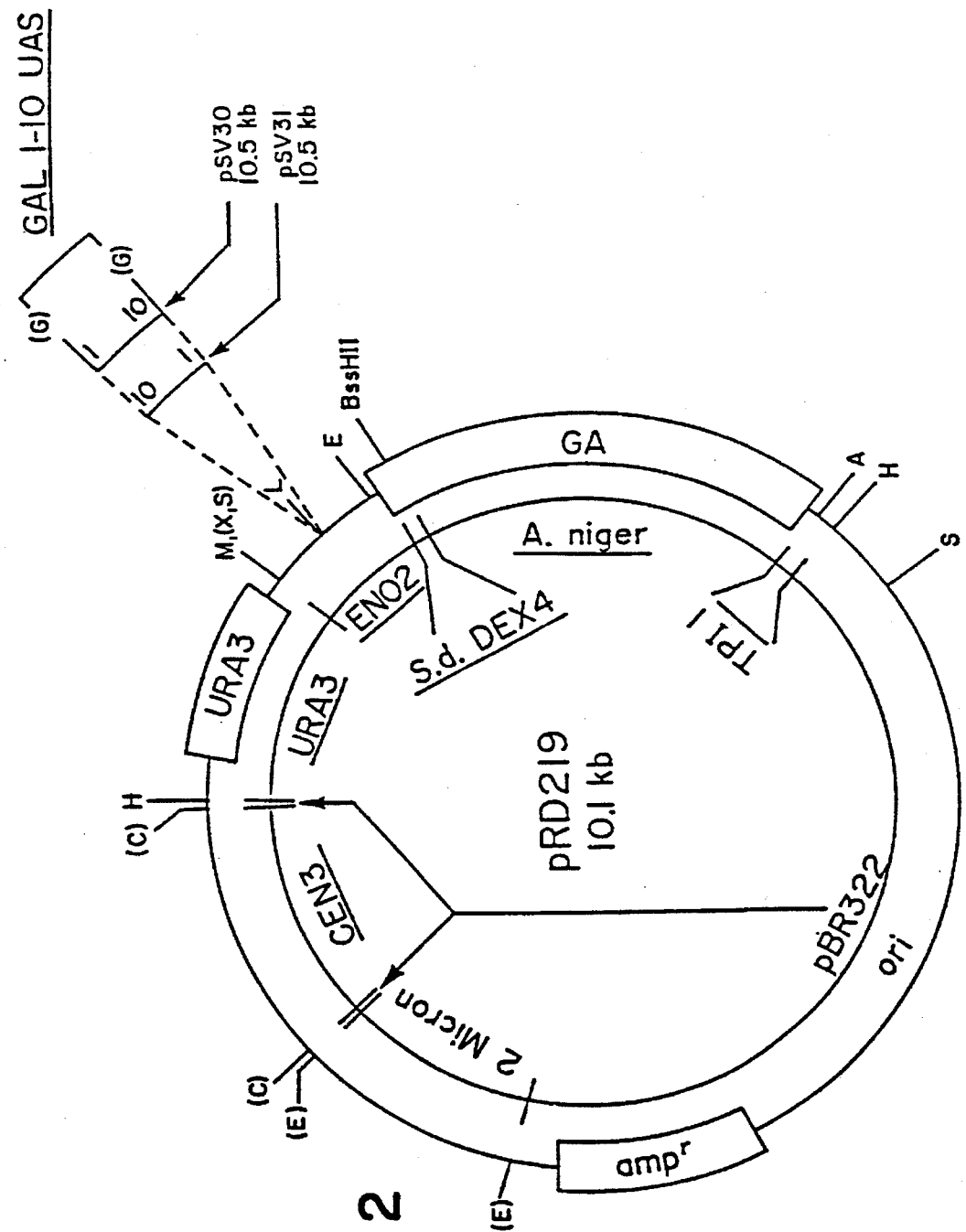

FIG. 2 is a diagrammatic representation of the plasmids pRD219, a derivative of pRD170 containing the *S. diastaticus* DEX4 signal peptide encoding sequence; pSV30, a derivative of pRD219 containing the GAL1,10 upstream activating sequence inserted into the ENO2promoter; and pSV31, which is identical to pSV30 except that the GAL1,10 upstream activating sequence is inserted in the opposite orientation.

FIG. 3 is the DNA sequence of a BglII fragment, containing the GAL1,10 upstream activating sequence, which was inserted into pRD219 to form pSV30 and pSV31.

Construction of pRD170

The first step in the construction of pRD170 (FIG. 1), in which the *A. niger* glucoamylase gene is under the transcriptional control of the ENO2 promoter, was the isolation of the ENO2 gene from *Saccharomyces cerevisiae*. Next, the ENO2 promoter was isolated and substituted for the TPI1 promoter in pRD158. Finally, the resultant vector, pRD170, was used to transform host *S. cerevisiae* cells. In more detail, these steps were carried out as follows. (All manipulations of DNA, *Escherichia coli* and *S. cerevisiae* were accomplished by routine techniques well known in the art (Maniatis et al. (1982) Molecular Cloning Cold Spring Harbor Laboratory Press; and Sherman et al. (1981) Methods in Yeast Genetics, Cold Spring Harbor Laboratory Press). All DNA coordinates given herein are relative to the ATG start codon of the relevant coding sequence, with the A of the ATG start codon designated as +1.)

Cloning of the ENO2 Gene

Based on the published sequence of the *S. cerevisiae* ENO2 gene, a single stranded oligonucleotide of 30 bases (+1 to +30 of the ENO2 gene) was synthesized on an Applied Biosystems model 380A as recommended by the manufacturer. The sequence of the synthetic oligonucleotide is 5'-ATGGCTGTCTCTAAAGTTTACGCTAGATCC-3'. This 30-mer was labeled with $^{32}$P at its 5' end and used as a hybridization probe to detect plasmids that contain the ENO2 gene from a genomic *S. cerevsiae* gene bank made in the vector YEP24 (Carlson and Botstein (1982) Cell 28: 145). The colony hybridization method was used to detect replica *E. coli* colonies containing the desired plasmid. The presence of the ENO2 gene and promoter on plasmid isolates was confirmed by demonstrating the presence of DNA restriction fragments predicted from the published DNA sequence, and by demonstrating over-production of a protein the size of enolase 2 from *S. cerevisiae* cells transformed by the plasmid. One particular plasmid isolated from the Carlson gene bank that contained the ENO2 gene was named pRD160.

Isolation of ENO2 Promoter

It was known from the literature that DNA sequences required for ENO2 promoter activity are located between a SalI site at about −600 base pairs and the beginning of the ENO2 coding sequence (Cohen et al. (1986) Mol. Cell Biol. 6: 2287). Therefore, the 750 base pair SalI to HindIII fragment that contained the ENO2 promoter activity and the first few bases of ENO2 coding sequence from pRD160 was purified by acrylamide gel electrophoresis. This fragment was then partially digested with DdeI, and the 550 base pair SalI to DdeI (partial) fragment was purified from other fragments, again by acrylamide gel electrophoresis. This SalI to DdeI (partial) fragment, together with a synthetic double stranded DNA fragment, were used to reconstitute the ENO2 promoter with a heterologous gene, the *Aspergillus niger* glucoamylase gene, as described below.

Expression of a Heterologous Gene from the ENO2 Promoter.

Referring to FIG. 1, the *S. cerevisiae* ENO2 promoter was substituted for the TPI1 promoter in plasmid pRD158, as described below. (Abbreviations for restriction sites in the Figures are as follows: A, XbaI; C, ClaI; E, EcoRI; G, BglII; H, HindIII; L, BclI; M, XmaI; X, XhoI; S,SalI. Parentheses indicate a former site destroyed during construction. Moving clockwise around, pRD158 contains the following DNA fragments: (1) HindIII to XmaI, the *S. cerevisiae* URA3 gene; (2) XmaI, XhoI, XmaI, a synthetic adapter with the sequence 5'-CCGGGCTCGAGCCGAGCTCGGGCC-5' that created a XhoI site between two XmaI sites; (3) XmaI to BglII, the *S. cerevisiae* TPI1 promoter, going from a naturally occurring MstII site (filled in) at −638 to a T residue at −44, followed by a synthetic DNA fragment of the following sequence:

5'-AGAATTCATCTATAACTACAAAAAACACATACATAAACTAAAAATGTCTTTCAGATCT-3'
3'-TCTTAAGTAGATATTGATGTTTTTTGTGTATGTATTTGATTTTTACAGAAAGTCTAGA-5'

(4) BglII to XbaI, a DNA copy of the *A. niger* glucoamylase gene (Boel et al. (1984) EMBO Journal 3: 1097). The BglII site was introduced artificially without changing the native amino acid sequence, and the XbaI site was inserted artificially at a natural BclI site (Boel et al., id.); (5) XbaI to HindIII, a 90 base pair fragment containing the TPI1 transcription terminator; (6) HindIII to (EcoRI), the majority of pBR322, with a 275 base pair SalI to BamHI deletion that leaves a SalI site but no BamHI site, and abolishes tetracycline resistance; (7) (EcoRI) to (EcoRI), an approximately 1000 base pair (XbaI) to (PstI) fragment containing the origin of replication from the endogenous S. cerevisiae 2 micron circle plasmid; (8) (EcoRI) to (ClaI), the short EcoRI to ClaI fragment of pBR322; (9) (ClaI) to (ClaI), an approximately 1200 base pair (ClaI) to (BamHI) fragment containing CEN3, the centromere from S. cerevisiae chromosome III; (10) (ClaI) to HindIII, the short ClaI to HindIII fragment of pBR322.

The XhoI to BglII fragment of pRD158 that contained the TPI1 promoter was substituted with the 550 base pair (SalI) to (DdeI) (partial) fragment described above, together with a synthetic 60/61-mer that contained sticky ends compatible with the DdeI and BglII sticky ends; the 60/61-mer has the sequence:

```
5'-TTAGTTTCTTTCATAACACCAAGCAACTAATACTATAACATACAATAATAATGTCTTTCA-3'
3'-   CAAAGAAAGTATTGTGGTTCGTTGATTATGATATTGTATGTTATTATTACAGAAAGTCTAG-5'
```

The resulting plasmid, containing the S. cerevisiae ENO2 promoter joined correctly to the glucoamylase gene via the synthetic fragment, was named pRD170. pRD170 was used to transform S. cerevisiae strain BWG 1–7A (Mata, leu 2–3, leu 2–112, his 4–519, ade 1–100, ura 3–52) (Guarente and Hoar (1984) Proc. Natl. Acad. Sci. USA 81: 7860) to URA3+. Transformants were grown to saturation in minimal selective medium containing 2% glucose (until all glucose had been consumed) and culture supernatants were assayed by incubating a mixture of 0.5 ml supernatant, 0.1 ml 1.0 M sodium citrate, pH 5.0, 0.2 ml 5% Difco soluble starch, and 0.3 ml water, at 50° C. for 0.2 to 12 hours. At appropriate times, a 25 microliter aliquot from each sample was assayed for released glucose with a Yellow Springs Instruments Glucose Analyzer according to the manufacturer. The pRD170-transformed cells exhibited high glucoamylase production as measured by this test.

Promoter Elements that Affect Heterologous Gene Expression

In S. cerevisiae, the best studied yeast, it is generally the case that a DNA fragment containing sequences from about −800 to +1 (relative to the A of the ATG of the start codon of the associated gene) will provide transcription and translation initiation, as well as mRNA stabilization, when the fragment is connected by ligation to a heterologous coding sequence. Usually such a promoter fragment contains sequences that confer not only the ability to bring about gene expression, but also sequences (called regulatory sequences) that affect the regulation of expression for the associated gene.

In addition, sometimes regulatory sequences can be found downstream from +1, as far as about +230. In some well-studied yeast promoters, the regulatory sequence is separated from the actual point (or points) at which mRNA transcription begins ("initiation points") by about 100 to 400 base pairs. (This is in contrast to the situation in E. coli where regulatory sequences are usually in close proximity (within about 20 base pairs) to the initiation points.) In yeast, if a regulatory sequence is upstream from the initiation points, it is called a UAS (upstream activation sequence) (see Guarente et al. (1982) Proc. Natl. Acad. Sci. U.S.A. 79: 7410). The UAS is usually between about 15 base pairs and 120 base pairs in length, and as mentioned above, often lies between −800 and the transcription initiation points. Unlike the situation for E. coli, the exact spacing between the UAS and initiation points is not critical, since it is known that UAS's can be moved tens or even hundreds of base pairs relative to transcription initiation points in either direction without abolishing UAS activity. Other sequences that are thought to play a role in expression of genes in yeast are 1) the so called "TATA" or "TATAA" sequence (which is located at −180 to −176 in S. cerevisiae ENO2), 2) the sequence CACACA or CATACA or a closely related sequence that is found between the initiation points and +1 of many highly expressed yeast genes (−12 to −7 in S. cerevisiae ENO2), 3) the sequences at the initiation points (in many yeast genes, transcription initiates at A residues), and 4) the sequences surrounding the ATG start codon. Many highly expressed Saccharomyces genes have an A at −3 and a G at +4, and G is statistically under-represented in the region upstream from the ATG (−1 to about −20). In yeast, except for "TATA", there is no consensus sequence for promoters or ribosome binding sites as in E. coli. Moreover, the precise spacing between sequence elements does not seem to be critical, since the distance between "TATA" and initiation points can vary from about 25 to 100 base pairs. All of the above-mentioned promoter elements can influence transcription, translation, or mRNA stability. Because of this fact, one can obtain advantages of the ENO2 promoters of this invention by using portions of the above-described ENO2 sequence of pRD170 in combination with other promoter elements derived from other sources. That such hybrid promoters can advantageously be made and used has been proven in the case of other yeast promoters, as follows.

As measured with lacZ fusions (Yocum et al. (1984) Mol. Cell. Biol. 4: 1985), a fully induced GAL10 promoter is about twice as strong as a fully induced CYC1 promoter (1800 vs. 900 units). However a hybrid promoter that substituted the GAL10 UAS for the CYC1 UAS, but retained the other 3 elements ("TATA", initiation points, and ATG region) of the CYC1 promoter was, when fully induced, almost twice as strong as the GAL10 promoter (3400 units). From this data one can conclude that the fully induced GAL10 UAS is more effective than the fully induced CYC1 UAS, but that the other three elements of CYC1 are more effective than the analogous sequences from GAL10, at least in the particular context of expressing the heterologous lacZ fusion.

Thus the entire ENO2 promoter region from −598 to +1, cloned as above, and used to express a heterologous gene, contains several smaller elements that will be useful in conjunction with other promoter elements from other promoters. For example, the ENO2 UAS is known to be situated between a SalI site at −598 and about −456. There is a BclI site at −315 and a BstXI site at −405. Thus the ENO2 UAS (by itself a "promoter" according to the definition used herein) can be easily obtained on a SalI to BclI or BstXI fragment and used to make hybrid promoters. For example, the TPI1 promoter has SphI and MstII sites at −225 and −638, respectively, which surround the TPI1 UAS. The ENO2 promoter could be substituted for the TPI1 UAS by ligating the ENO2 UAS (after blunting the ends) into the SphI to MstII gap suggested above (after blunting the ends).

Similarly, the *S. diastaticus* DEX1 gene (Yamashita et al. (1985) J. Bact. 161: 567) has a Sau3A site at −92 that could be ligated to the BclI site of the ENO2 promoter to give a hybrid ENO2-DEX1 promoter.

Conversely, after removal of the ENO2 UAS on an appropriate plasmid such as pRD170 by cutting with SmaI and BclI, a new UAS with desirable regulatory properties (for example, the *S. cerevisiae* GAL1,10 UAS) could be inserted (Guarente et al. (1982) Proc. Natl. Acad. Sci. 79: 7410) to give a hybrid promoter that utilizes the "TATA", initiation points, and ATG start codon region of the ENO2 promoter. Other appropriate UAS's are also useful in hybrid promoters; for example, the *S. carlsbergensis* GAL1,10 UAS (Citron et al., supra). It is also possible to construct a hybrid promoter that contains two or more ENO2 UAS's, or an ENO2 UAS plus a TPI1UAS, and so on.

Construction of the ENO2-GAL1,10 Hybrid Promoter

An ENO2-GAL1,10 hybrid promoter was constructed starting with the plasmid pRD219 (FIG. 2) which contains the ENO2 promoter fused to a glucoamylase gene. pRD219 is identical to pRD170 (above) with the exception of the junction region connecting the ENO2 promoter and the glucoamylase gene. The junction fragment consists of ENO2 promoter sequences derived from positions −50 to −1 (relative to translation initiation), followed by the DNA sequence coding for the *S. diastaticus* DEX4 gene signal peptide (described in Maine et al., U.S. Ser. No. 810,423, filed Dec. 18, 1985, assigned to the same assignee and hereby incorporated by reference). The presence of the DEX4 signal peptide encoding sequence allows for efficient secretion of the glucoamylase gene product. The junction fragment is a DdeI-BssHII 138/139-mer synthetic DNA fragment of the following sequence:

5'-TTAGAATTCTTTCATAACACCAAGCAACTAATACT
3'- CTTAAGAAAGTATTGTGGTTCGTTGATTATGA

ATAACATACAATAATAATGGCAAGACAAAAGATGTTTT
TATTGTATGTTATTATTACCGTTCTGTTTTCTACAAAA

ATAACAAATTACTCGGCATGCTCAGCGTAGGATT
TATTGTTTAATGAGCCGTACGAGTCGCATCCTAA

CGGGTTTGCTTGGGCGTTGGAAAACATTAAG-3'
GCCCAAACGAACCCGCAACCTTTTGTAATTCGCGC-5'

The ENO2-derived region of the synthetic DNA fragment contains a single base change and a single base insertion relative to the natural ENO2 gene sequence just 3' to the DdeI site, that results in the introduction of an EcoRI site. The junction fragment joins the DEX4 signal peptide encoding DNA to the *A. niger* glucoamylase gene (Boel, et al., id.) through a BssHII site.

The following strategy was used to insert the *S. cerevisiae* GAL1,10 UAS between the ENO2 UAS and the ENO2 TATA region of pRD219. The 365 bp DdeI-Sau3A fragment which contains the GAL1,10 UAS (See FIG. 3) (Guarente et al. (1982) Proc. Natl. Acad. Sci. USA 79: 7410; Yocum et al. (1984) Mol. Cell. Biol.4: 1985) was purified, its ends were made flush by filling in, and it was ligated to the large HindIII-AvaI fragment of pBR322, which had also had its ends filled in, to form the plasmid pRY20. In this construct, the HindIII and AvaI sites are regenerated. pRY20 was cut with AvaI, the ends were filled in, and it was ligated in the presence of 8 bp BglII linkers (New England Biolabs); the recircularized plasmid is pRY21. The same strategy was used to insert 8 bp BglII linkers at the HindIII site of pRY21, yielding pRY24. Finally, the approximately 375 bp BglII fragment of pRY24, containing the GAL1,10 UAS, was inserted in either orientation at the unique BclI site of pRD219, located at about position −316 relative to the translation initation codon of the DEX4-glucoamylase fusion gene, to form plasmids pSV30 and pSV31; pSV30 contains the GAL1,10 UAS oriented such that the GAL10 proximal end is closer to the glucoamylase gene, whereas pSV31 contains the GAL1,10 UAS in the opposite orientation.

pRD219, pSV30, and pSV31 were used to transform *S. cerevisiae* strain BWG 1–7A (MATa, leu2-3, leu2–112, his4-519, ade 1-100, ura3-52 GAL2) (Guarente and Hoar (1984) Proc. Natl. Acad. Sci., USA 81: 7860) to URA3+. Transformants were grown to saturation in minimal selective medium containing either 2% glucose or 2% galactose (until either all the glucose or all the galactose had been consumed), and the supernatants were assayed for glucoamylase activity as previously described. Glucoamylase activity was high in pRD219-transformed cells grown in glucose, but barely detectable in pSV30- and pSV31-transformed cells grown on glucose (see Table I), suggesting that the regulatory effects of the GAL1,10 UAS on glucoamylase expression are dominant over those of the ENO2 UAS. Glucose repression of the GAL1 and GAL10 genes is known to be mediated, at least in part, through sequences located in the GAL1,10 UAS (Yocum (1987) in Biological Research on Industrial Yeasts, Vol. III. eds. Stewart, Russell, Klein and Hiebsch (CRC Press, Boca Raton, Fla.), pp. 61–70.).

Growth on galactose instead of glucose resulted in a reduction of glucoamylase production in cells containing pRD219, but an induction of glucoamylase production in cells containing pSV30 and pSV31, further supporting the above conclusion that the GAL1,10 UAS is dominant over the ENO2 UAS, in this context. The orientation of the GAL1,10 UAS had an effect on the level of galactose-induced expression of the glucoamylase gene; pSV30-transformed cells reproducibly exhibited higher levels of glucoamylase activity when grown on galactose than pSV31-transformed cells. Glucoamylase activity was 3 and 2 fold higher, respectively, in pSV30- and pSV31-transformed cells grown on galactose than in pRD219-transformed cells grown on glucose. Thus, the use of a hybrid promoter containing two UAS sequences resulted in a significant improvement in glucoamylase production, as well as strict regulation of glucoamylase production in response to a carbon source.

The effect of copy number of the ENO2-GAL1,10-glucoamylase fusion gene on glucoamylase production and carbon source regulation was also determined. The plasmids pRD219, pSV30 and pSV31 contain a centromere and are therefore maintained at about one copy per haploid genome. pRD166 is a precursor of pRD170 which lacks centromeric sequences, and pSV46 and pSV47 are derivatives of pSV30 and pSV31, respectively, which also lack centromeric sequences; these plasmids contain a 2-micron circle origin of replication and are therefore present in high copy number in the cell. pRD226, pSV52 and pSV53 are integrating vectors used to introduce single copies of the glucoamylase gene into the yeast genome; these plasmids are derived from pRD170, pSV30 and pSV31, respectively. A cir° version of *S. cerevisiae* strain BWG 1–7A was used as a host yeast strain for experiments employing centromere plasmids and a cir⁺ version of this host strain was used for all other experiments.

Transformed cells were grown on either glucose or galactose and glucoamylase production was quantitated. Table 1 shows that when the hybrid ENO2-GAL1,10 promoter, containing two UAS sequences, directs expression of the glucoamylase gene, there is a significant increase in glucoamylase production, regardless of the copy number of the glucoamylase gene. pRD219, pRD166, and pRD226 do not contain the GAL1,10 UAS and produce approximately 2–3 fold less glucoamylase than the analogous GAL1,10 UAS-containing plasmids when fully induced. YEP24 does not contain a glucoamylase gene and, as expected, did not produce any glucoamylase. In addition, glucoamylase production in plasmids containing the GAL1,10 UAS, regardless of glucoamylase gene copy number, was induced by galactose, whereas plasmids lacking the GAL1,10 UAS, i.e. containing only the ENO2 UAS, were induced most efficiently, but not only, by glucose.

TABLE 1

| Plasmid | Type | Orientation of GAL1,10 UAS | Glucoamylase Activity* Glucose | Activity* Galactose |
|---|---|---|---|---|
| pRD219 | centromere | — | 121 | 58 |
| pSV30 | centromere | GAL10 | 0 | 370 |
| pSV31 | centromere | GAL1 | 1 | 241 |
| pRD166 | 2-micron | — | 254 | 150 |
| pSV46 | 2-micron | GAL10 | 2 | 493 |
| pSV47 | 2-micron | GAL1 | 4 | 299 |
| pRD226 | integrating | — | 53 | 21 |
| pSV52 | integrating | GAL10 | 0 | 234 |
| pSV53 | integrating | GAL1 | 1 | 137 |
| YEP24 | 2-micron | — | 1 | 0 |

*arbitrary units

Construction of an ENO2-GAL1,10-PDGF fusion

The galactose inducible hybrid promoters containing ENO2 and GAL1,10 UAS sequences have also been used to express and secrete the human platelet-derived growth factor (PDGF) from yeast.

The ENO2 promoter for pRD219 or the hybrid promoters of pSV30 and pSV31 were placed in front of a hybrid gene encoding the DEX4 signal sequence fused in frame to PDGF coding sequences on autonomously replicating 2-micron based plasmids containing the selectable URA3 gene, to give pAP275A, pSV43, and pSV44, respectively. All three plasmids were transformed into a ura3⁻ haploid yeast by standard methods and the transformants were innoculated into 10 ml of minimal selective medium lacking uracil and containing either 2% glucose or 0.5% glucose plus 5% galactose as a carbon source. After 72 hours of growth at 30° C., the cells were removed and the culture supernatants were assayed for PDGF by Western blot using commercial anti-PDGF antibody (Collaborative Research, Waltham, Mass.). The level of secreted PDGF was estimated by comparison with a sample of PDGF isolated from human blood (Collaborative Research). As shown in Table 2, higher levels of PDGF were produced when the hybrid promoter directs expression of the PDGF gene than when the ENO2 promoter directs PDGF gene expression. The highest level of PDGF gene expression occurs when the GAL1 proximal end of the GAL1,10 UAS is oriented toward the PDGF gene (pSV44).

The presence of the plasmid pAP275A, which contains the PDGF gene under control of the ENO2 promoter, proved deleterious to growth of the transformed cell when glucose was the carbon source, presumably as a result of high level constitutive ENO2-promoted PDGF gene expression in the presence of the ENO2-inducer (i.e., glucose). Use of the regulated hybrid promoters (pSV43, pSV44) and growth of transformants in a mixture of glucose and galactose alleviated this problem. In the latter case, the hybrid promoter is glucose repressed in the early stages of fermentation and transformants grow at a normal rate and produce little or no PDGF; as the glucose is depleted later in fermentation, the hybrid promoter is derepressed by the lack of glucose and induced by galactose, leading to high levels of PDGF. Thus, the use of hybrid promoters containing strictly regulated promoters is clearly advantageous when expressing at high level a gene that hinders cell growth.

TABLE 2

| Plasmid | Carbon source | Growth Rate | Secreted PDGF |
|---|---|---|---|
| pAP275A | 2% glucose | poor | 120 ng/ml |
| pSV43 | 0.5% glucose/ 5% galactose | good | 800 ng/ml |
| pSV44 | 0.5% glucose/ 5% galactose | good | 1200 ng/ml |

Hybrid promoters containing multiple UAS sequences may be useful for other applications. For instance, the glucoamylase gene on pRD219 could be made maltose-inducible by inserting the maltose UAS ($UAS_M$) at the BclI site. The $UAS_M$ mediates induction of the maltase (MALS) and maltose permease (MALT) genes of S. cerevisiae by maltose (Hong and Marmur (1987) Mol Cell. Biol. 1: 247). A maltose-inducible glucoamylase gene could then be introduced into brewing strains of Saccharomyces to produce low calorie beer, or into distillery strains of Saccharomyces to increase carbohydrate utilization and ethanol yield.

It is possible to further subdivide the ENO2 promoter into individual functional sequences such as "TATA", initiation points, and ATG start codon region. Prepared as either restriction enzyme produced fragments or as synthetic oligonucleotides, these sequences could be substituted for the analogous sequence in other promoters, and such hybrid promoters may have desirable properties such as increased strength.

Deposit

E. coli K12, strain YMC9, transformed with pRD170 was deposited in the American Type Culture Collection on Apr. 10, 1987, and was assigned the accession number 67385.

Applicants' assignee, BioTechnica International, Inc., represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commisssioner to be entitled thereto under 37 CFR 1.15 and 35 USC 122. The deposited material will be maintained with all the care necessary to keep it viable and uncontaminated for a period of at least five years after the most recent request for the furnishing of a sample of the deposited microorganism, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit. A copy of the A.T.C.C. Budapest Treaty deposit receipt is attached to this application.

We claim:

1. A DNA sequence comprising a hybrid yeast promoter fused to a heterologous gene, said hybrid yeast promoter comprising an ENO2 promoter, wherein said ENO2 promoter includes the upstream activating sequence and TATA region naturally associated with said ENO2 promoter, and an additional upstream activating sequence derived from a yeast promoter operably fused to said ENO2 promoter, wherein said additional upstream activating sequence is located between said ENO2 upstream activating sequence and TATA region.

2. The DNA sequence of claim 1 wherein said additional upstream activating sequence is derived from a yeast promoter other than said ENO2 promoter.

3. The DNA sequence of claim 1 wherein said additional upstream activating sequence is derived from an ENO2 promoter.

4. The DNA sequence of claim 1, wherein said additional upstream activating sequence is a GAL1,10 upstream activating sequence having a GAL1-proximal end and a GAL10-proximal end.

5. The DNA sequence of claim 4, wherein said GAL1-proximal end is closest to said heterologous gene.

6. The DNA sequence of claim 4, wherein said GAL10-proximal end is closest to said heterologous gene.

7. The DNA sequence of claim 4, wherein said GAL1,10 upstream activating sequence is derived from the GAL1,10 DNA sequence of yeast of the genus Saccharomyces.

8. The DNA sequence of claim 7, wherein said yeast is *S. cerevisiae*.

9. A yeast cell transformed with the DNA sequence of claim 1.

10. The yeast cell of claim 9, wherein yeast is of the genus Saccharomyces.

11. A plasmid vector comprising the DNA sequence of claim 1, wherein said vector is capable of transforming a host yeast cell.

12. The DNA sequence of claim 1, wherein said heterologous gene encodes a glucoamylase.

13. The vector pSV30.

14. The vector pSV31.

15. A method of producing a protein other than enolase 2 comprising growing a yeast cell transformed with a vector of claim 11.

* * * * *